(12) United States Patent
Miranda Utrera et al.

(10) Patent No.: US 11,401,556 B2
(45) Date of Patent: Aug. 2, 2022

(54) PROGNOSTIC METHOD FOR DETERMINING THE RISK OF RELAPSE IN RENAL CANCER PATIENTS WITH A CLEAR CELL TYPE OF RENAL CARCINOMA, STAGES I AND II, AND KIT FOR SAME

(71) Applicants: FUNDACIÓN PARA LA INVESTIGACIÓN BIOMEDICA DEL HOSPITAL 12 DE OCTUBRE, Madrid (ES); FUNDACIÓN PARA LA INVESTIGACIÓN BIOMEDICA DEL HOSPITAL UNIVERSITARIO LA PAZ, Madrid (ES)

(72) Inventors: Natalia Miranda Utrera, Madrid (ES); Felipe Villacampa Aubá, Madrid (ES); Daniel Castellano, Madrid (ES); Juan Angel Fresno Vara, Madrid (ES); Angelo Gámez Pozo, Madrid (ES)

(73) Assignees: FUNDACIÔN PARA LA INVESTIGACIÔN BIOMEDICA DEL HOSPITAL 12 DE OCTUBRE, Madrid (ES); FUNDACION PARA LA INVESTIGACION BIOMEDICA DEL HOSPITAL UNIVERSITARIO LA PAZ (FIBHULP), Madrid (ES)

( * ) Notice: Subject to any disclaimer, the term of this patent is extended or adjusted under 35 U.S.C. 154(b) by 1141 days.

(21) Appl. No.: 15/761,687

(22) PCT Filed: Sep. 23, 2016

(86) PCT No.: PCT/EP2016/072723
§ 371 (c)(1),
(2) Date: Mar. 20, 2018

(87) PCT Pub. No.: WO2017/050985
PCT Pub. Date: Mar. 30, 2017

(65) Prior Publication Data
US 2018/0346990 A1 Dec. 6, 2018

(30) Foreign Application Priority Data
Sep. 23, 2015 (ES) ................. ES201531360

(51) Int. Cl.
*C12Q 1/6886* (2018.01)
*C12Q 1/6837* (2018.01)
*G16H 10/40* (2018.01)
*G16H 50/30* (2018.01)

(52) U.S. Cl.
CPC ........ *C12Q 1/6886* (2013.01); *C12Q 1/6837* (2013.01); *G16H 10/40* (2018.01); *G16H 50/30* (2018.01); *C12Q 2600/118* (2013.01); *C12Q 2600/158* (2013.01); *C12Q 2600/178* (2013.01); *G01N 2800/54* (2013.01)

(58) Field of Classification Search
None
See application file for complete search history.

(56) References Cited

U.S. PATENT DOCUMENTS

2012/0108466 A1  5/2012  Wu et al.

FOREIGN PATENT DOCUMENTS

| WO | WO 2010/145035 A1 | 12/2010 |
| WO | WO 2011/039757 A2 | 4/2011 |
| WO | WO 2013/026684 A1 | 2/2013 |

OTHER PUBLICATIONS

Escudier et al. Sequential Therapy in Renal Cell Carcinoma Cancer vol. 115, pp. 2321-2326 (Year: 2009).*
Geo Database Accession No. GPL10656, Jul. 8, 2010, 2 pages.
Slaby et al., "Identification of MicroRNAs associated with early relapse after nephrectomy in renal cell carcinoma patients," *Genes, Chromosomes & Cancer*, vol. 51, pp. 707-716, 2012.
Vergho et al., "Combination of expression levels of miR-21 and miR-126 is associated with cancer-specific survival in clear-cell renal cell carcinoma," *BMC Cancer*, 14:25, 2014 (10 pages).
Hildebrandt et al., "Hsa-miR-9 methylation status in associated with cancer development and metastatic recurrence in patients with clear cell renal cell carcinoma," *Oncogene*, vol. 29, pp. 5724-5728, 2010.
Li et al., "MicroRNAs in renal cell carcinoma: A systematic review of clinical implications (Review)," *Oncology Reports*, vol. 33, pp. 1571-1578, 2015.

* cited by examiner

*Primary Examiner* — John S Brusca
(74) *Attorney, Agent, or Firm* — Klarquist Sparkman, LLP

(57) ABSTRACT

A prognostic method, and a kit, for determining the risk of relapse of renal cancer of the clear cell renal carcinoma type, stages I and II, in a human subject; comprised of: (a) determining, in a tumor sample (biopsy) from the human subject, the levels of expression of the microRNAs hsa-miR-223, hsa-miR-103, hsa-miR-107, hsa-miR-425, hsa-miR-340, hsa-miR-130b, hsa-miR-652, hsa-miR-214, and hsa-miR-204; (b) determining a value which depends on the levels of expression of the microRNAs; and (c) determining the risk of relapse in renal cancer of the clear cell renal carcinoma type, in stages I and II, in the said human subject, by comparing the value obtained in step (b) with a cut-off value.

3 Claims, 2 Drawing Sheets
Specification includes a Sequence Listing.

SEQUENCE LISTING

```
<160> NUMBER OF SEQ ID NOS: 9

<210> SEQ ID NO 1
<211> LENGTH: 22
<212> TYPE: RNA
<213> ORGANISM: Artificial Sequence
<220> FEATURE:
<223> OTHER INFORMATION: hsa-miR-223

<400> SEQUENCE: 1
cguguauuug acaagcugag uu                                              22

<210> SEQ ID NO 2
<211> LENGTH: 23
<212> TYPE: RNA
<213> ORGANISM: Artificial Sequence
<220> FEATURE:
<223> OTHER INFORMATION: hsa-miR-103

<400> SEQUENCE: 2
agcagcauug uacagggcua uga                                             23

<210> SEQ ID NO 3
<211> LENGTH: 23
<212> TYPE: RNA
<213> ORGANISM: Artificial Sequence
<220> FEATURE:
<223> OTHER INFORMATION: hsa-miR-107

<400> SEQUENCE: 3
agcagcauug uacagggcua uca                                             23

<210> SEQ ID NO 4
<211> LENGTH: 23
<212> TYPE: RNA
<213> ORGANISM: Artificial Sequence
<220> FEATURE:
<223> OTHER INFORMATION: hsa-miR-425

<400> SEQUENCE: 4
aaugacacga ucacucccgu uga                                             23

<210> SEQ ID NO 5
<211> LENGTH: 22
<212> TYPE: RNA
<213> ORGANISM: Artificial Sequence
<220> FEATURE:
<223> OTHER INFORMATION: hsa-miR-340

<400> SEQUENCE: 5
uuauaaagca augagacuga uu                                              22

<210> SEQ ID NO 6
<211> LENGTH: 21
<212> TYPE: RNA
<213> ORGANISM: Artificial Sequence
```

```
<220> FEATURE:
<223> OTHER INFORMATION: hsa-miR-130b

<400> SEQUENCE: 6
acucuuuccc uguugcacua c                                              21

<210> SEQ ID NO 7
<211> LENGTH: 25
<212> TYPE: RNA
<213> ORGANISM: Artificial Sequence
<220> FEATURE:
<223> OTHER INFORMATION: hsa-miR-652

<400> SEQUENCE: 7
caacccuagg agagggugcc auuca                                          25

<210> SEQ ID NO 8
<211> LENGTH: 22
<212> TYPE: RNA
<213> ORGANISM: Artificial Sequence
<220> FEATURE:
<223> OTHER INFORMATION: hsa-miR-214

<400> SEQUENCE: 8
ugccugucua cacuugcugu gc                                             22

<210> SEQ ID NO 9
<211> LENGTH: 21
<212> TYPE: RNA
<213> ORGANISM: Artificial Sequence
<220> FEATURE:
<223> OTHER INFORMATION: hsa-miR-204

<400> SEQUENCE: 9
gcugggaagg caaagggacg u                                              21
```

PROGNOSTIC METHOD FOR DETERMINING THE RISK OF RELAPSE IN RENAL CANCER PATIENTS WITH A CLEAR CELL TYPE OF RENAL CARCINOMA, STAGES I AND II, AND KIT FOR SAME

CROSS REFERENCE TO RELATED APPLICATIONS

This is the § 371 U.S. National Stage of International Application No. PCT/EP2016/072723, filed Sep. 23, 2016, which was published in English under PCT Article 21(2), which in turn claims the benefit of ES Application No. P201531360, filed Sep. 23, 2015, which is incorporated herein in its entirety.

FIELD OF THE INVENTION

The present invention relates to means of prognostication in renal cancer of the clear cell renal carcinoma type. More particularly, the invention relates to prognostication in this type of cancer for determining the risk of relapse, employing a group of 9 RNA molecules (also referred to as "microRNAs" or "miRNAs").

BACKGROUND TO THE INVENTION

Clear cell renal carcinoma (CCRC) has an incidence of 11 cases per 100,000 persons, with a specific cancer mortality of ca. 35%.

In recent years, various drugs have demonstrated clinical utility in CCRC (stages III and IV), and some of these (such as sunitinib, sorafenib, everolimus, axitinib, and temsirolimus) have received approval for use in treating metastatic cancer in distinct therapeutic lines. The impact of these drugs on the natural history of advanced CCRC has led to initiation of numerous clinical trials to assess whether their use in adjuvant therapy can offer a benefit to patients. Most of these trials were focused on high risk populations (stages and high risk patients with stage II), but current parameters are inadequate to identify the patients at high risk for relapse.

In moderate stages of the disease (stages I and II), current treatment consists of complete excision of the tumor; also, recently some alternatives have been developed which involve ablative therapies in situ. In moderate stages, drugs are not employed as an adjuvant therapy. CCRC in moderate stages has an overall relapse rate of ca. 15%, and accordingly more than 85% of patients with localized stages will not benefit from adjuvant therapy.

WO2011039757A2 describes prognosis of CCRC with the use of miRNAs as markers. In that document, the miRNA hsa-miR-204 is described.

That document does not disclose the group comprising 9 miRNAs according to the present invention, and does not disclose a prognostic method which allows one to identify the risk of relapse of CCRC.

WO2010145035A1 describes the use of some of the miRNAs according to the present invention as markers for renal cancer of the CCRC type.

That document does not disclose the group comprising 9 miRNAs according to the present invention, and does not disclose a prognostic method which allows one to identify the risk of relapse of CCRC.

WO2013026684A1 discloses a prognostic and diagnostic method for renal cancer of the CCRC type which utilizes the expression profile of at least two miRNAs of a long list of miRNAs (FIG. 7 of WO2013026684A1).

That document describes the 9 miRNAs according to the present invention, but not a group of 9 miRNAs. Further, that document does not disclose a prognostic method which allows one to identify the risk of relapse of CCRC, and does not provide grounds for use of a group of the 9 miRNAs according to the present invention in a prognostic method which allows one to identify the risk of relapse of CCRC.

None of the three documents cited provides any grounds for devising the invention as set forth in the claims.

The cited documents, individually and in combination, do not suggest the claimed matter.

The objective technical problem of the invention in relation to the closest state of the art may be defined as that of devising a prognostic method to determine the risk of relapse of renal cancer of the CCRC type in stages I and II of the disease.

This problem is solved by a prognostic method for determining the risk of relapse of renal cancer of the CCRC type in localized stages I and II of the disease, as said method is set forth in the claims of the present application.

DESCRIPTION OF THE INVENTION

In a first aspect, the present invention provides prognostic method for determining the risk of relapse of renal cancer of the clear cell renal carcinoma type, stages I and II, in a human subject; comprising:

(a) determining, in a tumor sample (biopsy) from the human subject, the levels of expression of at least three microRNAs selected from the group consisting of: hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9;

(b) determining a value which depends on the levels of expression of said at least three microRNAs;

(c) determining the risk of relapse in renal cancer of the CCRC type, in stages I and II, in the said human subject, by comparing the value obtained in step (b) with a cut-off value.

In certain embodiments, the said at least three microRNAs comprise: hsa-miR-223 (SEQ ID NO: 1), hsa-miR-103 (SEQ ID NO: 2) and hsa-miR-107 (SEQ ID NO: 3).

In certain embodiments, said at least three microRNAs comprise at least four, at least five, at least six, at least seven, or at least eight of the microRNAs of the group consisting of: hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9.

In certain embodiments, said at least three microRNAs comprise all nine of the microRNAs of the group consisting of: hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9.

In certain embodiments, determining said value in step (b) comprises deriving a prediction score by summing the weighted expression level of each of said microRNAs, wherein the expression level for each of said microRNAs is as determined in step (a), and wherein the weighting applied to each respective microRNA expression level is a coefficient, as follows:

for hsa-miR-223 $w_i$ is 0.098392±5%;
for hsa-miR-103 $w_i$ is 0.045806±5%;

for hsa-miR-107 $w_i$ is 0.045869±5%;
for hsa-miR-425 $w_i$ is 0.163188±5%;
for hsa-miR-340* $w_i$ is 0.495063±5%;
for hsa-miR-130b $w_i$ is 0.374902±5%;
for hsa-miR-652 $w_i$ is 0.311327±5%;
for hsa-miR-214 $w_i$ is −0.064772±5%; and
for hsa-miR-204 $w_i$ is −0.220399±5%.

In certain embodiments, deriving said prediction score comprises summing the weighted expression level of each of said microRNAs according to the following formula:

$$\Sigma_i w_i x_i - 2{,}896{,}583,$$

where $w_i$ is the weight, and $x_i$ is the expression value of the microRNA i, and wherein:
for hsa-miR-223 $w_i$ is 0.098392
for hsa-miR-103 $w_i$ is 0.045806
for hsa-miR-107 $w_i$ is 0.045869
for hsa-miR-425 $w_i$ is 0.163188
for hsa-miR-340* $w_i$ is 0.495063
for hsa-miR-130b $w_i$ is 0.374902
for hsa-miR-652 $w_i$ is 0.311327
for hsa-miR-214 $w_i$ is −0.064772; and
for hsa-miR-204 $w_i$ is −0.220399.

In certain embodiments, said cut-off value is 0.954±5%, in particular, said cut-off value may be 0.954, and wherein:
if the value obtained in step (b) is greater than said cut-off value, said human subject is classified as being at high risk of relapse of renal cancer of the clear cell renal carcinoma type;
if the value obtained in step (b) is less than or equal to said cut-off value, said human subject is classified as being at low risk of relapse of renal cancer of the clear cell renal carcinoma type.

In certain embodiments, the level of expression of said microRNAs is determined with the use of at least one microarray of microRNAs. In this context, the microarray generally comprises a planar support having arranged thereon a plurality of oligonucleotide sequences that comprise miRNA sequences or which are complementary to miRNA sequences thereby acting as probes to capture specific miRNA sequences from an RNA-containing sample.

In particular, the present invention provides a prognostic method for determining the risk of relapse in patients with renal cancer of the CCRC type in stages I and II, comprising:
(a) determining, in a tumor sample (biopsy) from the human subject, the level [(levels)] of expression of the microRNAs hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NO: 1-9;
(b) determining a value which depends on the levels of expression of the microRNAs hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NO: 1-9;
(c) determining the risk of relapse in renal cancer of the CCRC type, in stages I and II, in the said human subject, by comparing the value obtained in step (b) with a cut-off value.

This prognostic method enables identification of a high risk population for relapse, in localized stages of the disease (CCRC in stages I and II), whereby one can offer adjuvant treatment only to patients who require it.

According to another embodiment in connection with the first aspect of the invention, the level of expression is determined with the use of microarrays of microRNAs.

In a second aspect, the present invention provides a prognostic and treatment method for determining the risk of relapse of renal cancer of the clear cell renal carcinoma type, stages I and II, in a human subject and subsequently treating said subject, the method comprising:
(a) determining, in a tumor sample (biopsy) from the human subject, the level of expression of each of the microRNAs: hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9;
(b) determining a value which depends on the levels of expression of said microRNAs;
(c) determining the risk of relapse in renal cancer of the CCRC type, in stages I and II, in the said human subject, by comparing the value obtained in step (b) with a cut-off value, and
(d) (i) if the value obtained in step (b) is greater than said cut-off value, classifying said human subject as being at high risk of relapse of renal cancer of the clear cell renal carcinoma type and subsequently administering a therapeutically effective amount of sunitinib, sorafenib, everolimus, axitinib, and/or temsirolimus to said human subject as an adjuvant therapy; or
(ii) if the value obtained in step (b) is lower than said cut-off value, classifying said human subject as being at low risk of relapse of renal cancer of the clear cell renal carcinoma type and avoiding adjuvant therapy.

In a third aspect, the present invention provides a computational prognostic method for determining the risk of relapse of renal cancer of the clear cell renal carcinoma type, stages I and II, in a human subject; comprising:
(a) providing a patient data record containing the determined expression level of each of the microRNAs hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9, wherein said microRNA expression levels have been determined in a tumor sample (biopsy) from the human subject,
(b) providing a data processor,
(c) causing the data processor to process the patient data record to derive a prediction score by summing the weighted expression level of each of said microRNAs, according to the following formula:

$$\Sigma_i w_i x_i - 2{,}896{,}583,$$

where $w_i$ is the weight, and $x_i$ is the expression value of the microRNA i, and wherein:
for hsa-miR-223 $w_i$ is 0.098392;
for hsa-miR-103 $w_i$ is 0.045806;
for hsa-miR-107 $w_i$ is 0.045869;
for hsa-miR-425 $w_i$ is 0.163188;
for hsa-miR-340* $w_i$ is 0.495063;
for hsa-miR-130b $w_i$ is 0.374902;
for hsa-miR-652 $w_i$ is 0.311327;
for hsa-miR-214 $w_i$ is −0.064772; and
for hsa-miR-204 $w_i$ is −0.220399,
(d) determining the risk of relapse of renal cancer of the CCRC type, in stages I and II, in the said human subject, by comparing the prediction score obtained in step (c) with a cut-off value wherein:

if the value obtained in step (c) is greater than said cut-off value, said human subject is classified as being at high risk of relapse of renal cancer of the clear cell renal carcinoma type;

if the value obtained in step (c) is less than said cut-off value, said human subject is classified as being at low risk of relapse of renal cancer of the clear cell renal carcinoma type.

In certain embodiments, said cut-off value is 0.954±5% or is 0.954.

In a fourth aspect, the present invention provides a kit for realizing the prognostic method according to the first aspect of the invention, comprising reagents for determining the expression of the microRNAs hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NO: 1-9, in a tumor sample (biopsy) from a patient.

According to another embodiment in connection with the fourth aspect of the invention, the kit is comprised of a microarray of microRNAs or probes for microRNAs.

In some cases, at least 30%, 40%, 50%, 60%, 70%, 80% or at least 90% of the microRNAs, or probes thereto, present on said at least one microarray are selected from the group consisting of: hsa-miR-223, hsa-miR-103, hsa-miR-107, hsa-miR-425, hsa-miR-340, hsa-miR-130b, hsa-miR-652, hsa-miR-214, and hsa-miR-204. In this way the microarray may be enriched for those miRNAs or probes thereto that are informative for the prognostic and related methods of the present invention. Being enriched for informative miRNAs addresses a problem with commercially available miRNA microarrays that interrogate many thousands of different miRNAs most of which will not be informative for prognosis of CCRC relapse, the efficiency of which may be sub-optimal for carrying out the prognostic methods of the present invention.

It is further specified that the miRNAs correspond to each of the sequences in the following list of sequences:

The Sequence Listing is submitted as an ASCII text file in the form of the file named Sequence_Listing.txt, which was created on Mar. 20, 2018, and is 2213 bytes, which is incorporated by reference herein.

SEQ ID NO 1: hsa-miR-223
SEQ ID NO 2: hsa-miR-103
SEQ ID NO 3: hsa-miR-107
SEQ ID NO 4: hsa-miR-425
SEQ ID NO 5: hsa-miR-340*
SEQ ID NO 6: hsa-miR-130b
SEQ ID NO 7: hsa-miR-652
SEQ ID NO 8: hsa-miR-214
SEQ ID NO 9: hsa-miR-204.

FREE TEXT OF THE LIST OF SEQUENCES

Below, a transcription of the free text which appears in the list of sequences is provided:

SEQ ID NO 1:
hsa-miR-223:      CGUGUAUUUG ACAAGCUGAG UU

SEQ ID NO 2:
hsa-miR-03:       AGCAGCAUUG UACAGGGCUA UGA

SEQ ID NO 3:
hsa-miR-107:      AGCAGCAUUG UACAGGGCUA UCA

SEQ ID NO 4:
hsa-miR-425:      AAUGACACGA UCACUCCCGU UGA

SEQ ID NO 5:
hsa-miR-340*:     UUAUAAAGCA AUGAGACUGA UU

SEQ ID NO 6:
hsa-miR-130b:     ACUCUUUCCC UGUUGCACUA C

SEQ ID NO 7:
hsa-miR-652:      CAACCCUAGG AGAGGGUGCC AUUCA

SEQ ID NO 8:
hsa-miR-214:      UGCCUGUCUA CACUUGCUGU GC

SEQ ID NO 9:
hsa-miR-204:      GCUGGGAAGG CAAAGGGACG U.

The present invention includes the combination of the aspects and preferred features described except where such a combination is clearly impermissible or is stated to be expressly avoided. These and further aspects and embodiments of the invention are described in further detail below and with reference to the accompanying examples and figures.

EXAMPLES

Figure 1:
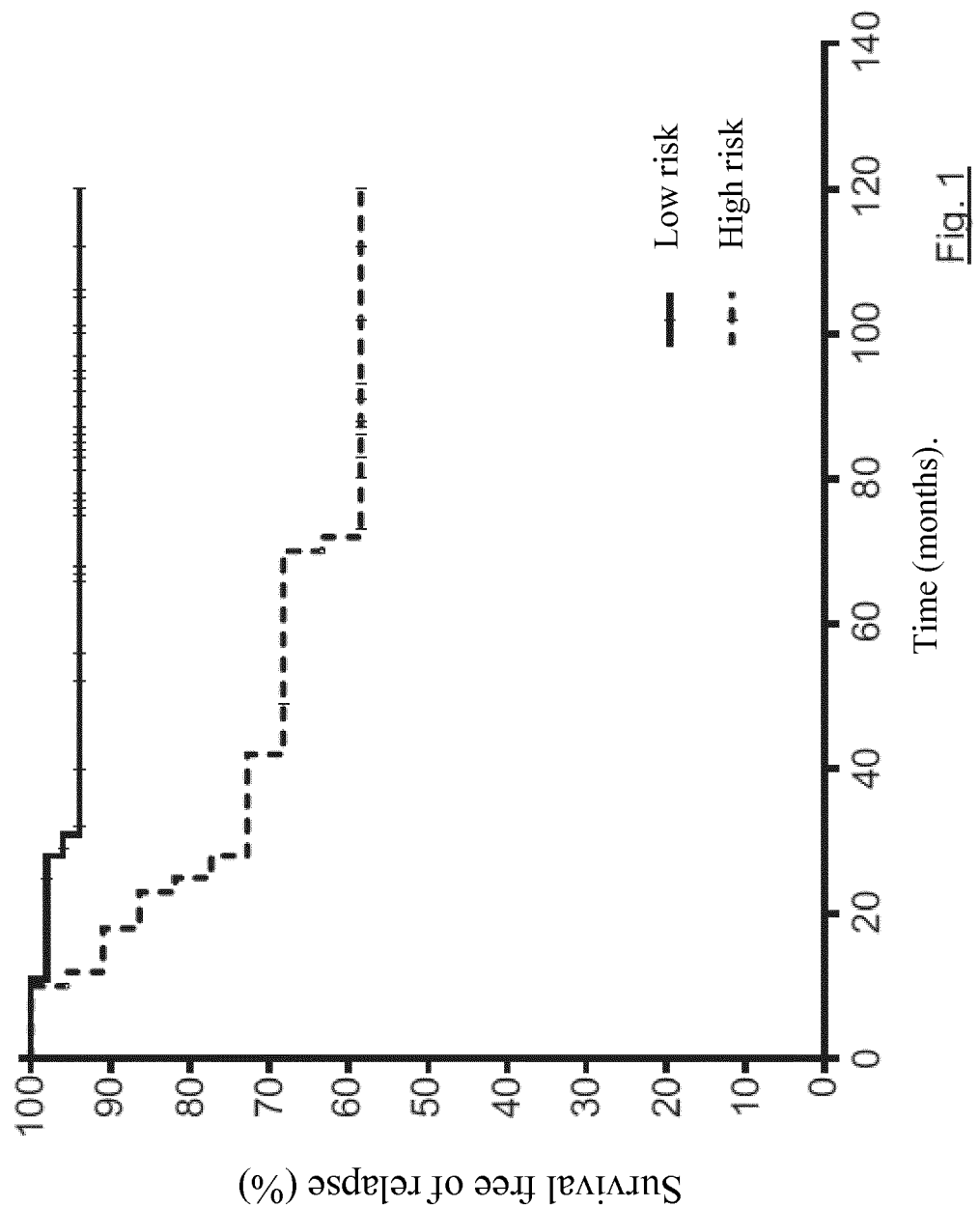
FIG. 1. Disease-free survival for various risk groups. The 5-year survival was 93.9% for patients at low risk, and 61.54% for patients at high risk (hazard ratio HR=12.1, p=0.0001) (confidence interval CI=3.012-37.92).
Figure 2:
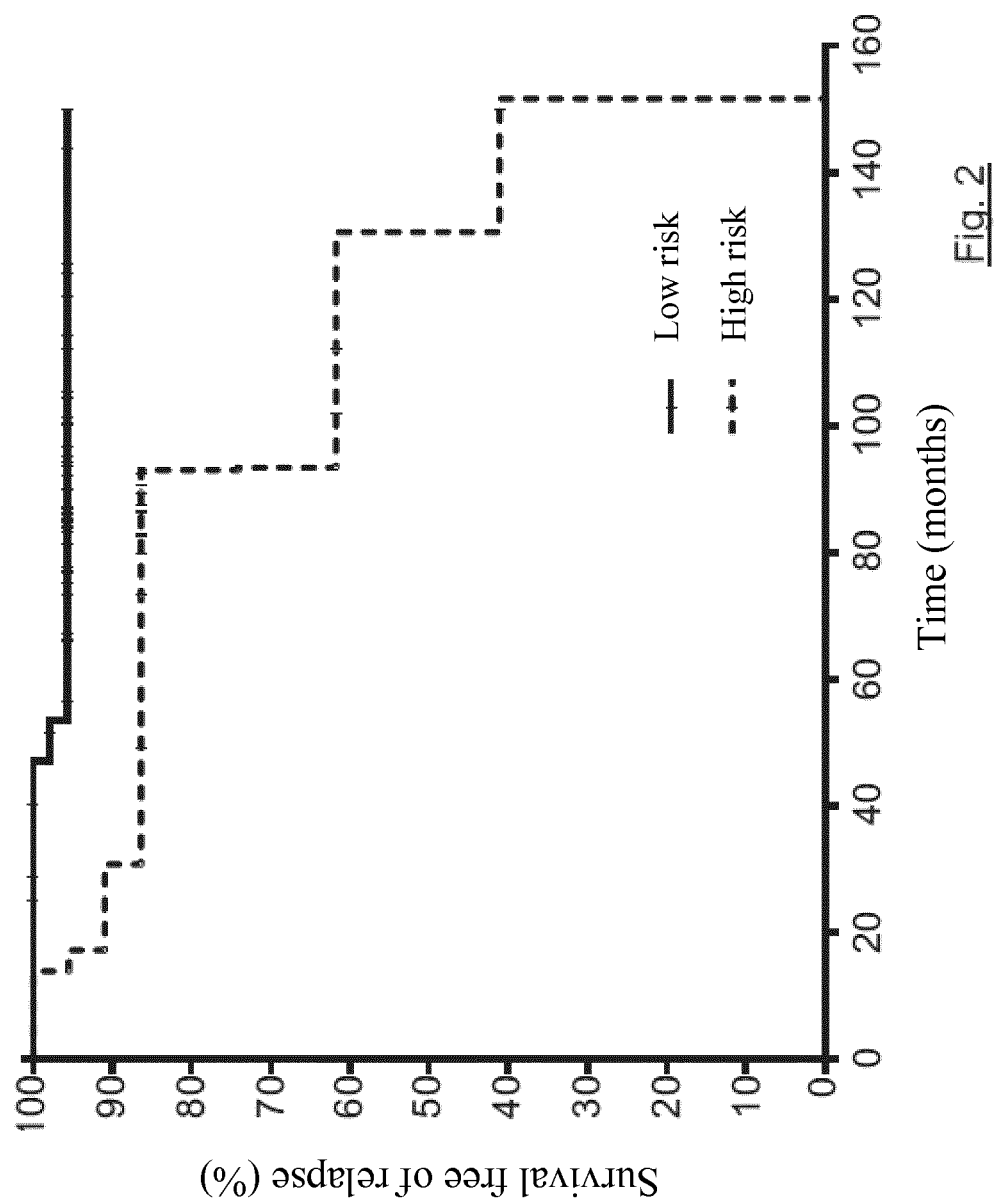
FIG. 2. Cancer-specific survival (CSS) for various risk groups. The 5-year CSS was 95.7% for patients at low risk, and 86.4% for patients at high risk (HR=7.7, p=0.0084) (CI=1.687-35.14).

Example 1. Design of the Study, and Cohort of Patients

An observational study was carried out which included all of the radical and partial nephrectomies performed at "October 12" University Hospital, of Madrid, between the year 1999 and 2008.

All patients who underwent radical or partial nephrectomies, open or laparoscopic, between 1999 and 2008, were included in the study.

For the staging, the TNM system was employed, which is the most commonly accepted classification. This classification was last modified in 2010.

TABLE 1

TNM Classification

| | |
|---|---|
| T: | Primary tumor: |
| Tx: | Primary tumor cannot be evaluated. |
| T0: | No evidence of a primary tumor. |
| T1: | Primary tumor <7 cm in major diameter, confined to kidney. |
| T1a: | Primary tumor <4 cm in major diameter, confined to kidney. |
| T1b: | Primary tumor >4 cm and <7 cm in major diameter, confined to kidney. |
| T2: | Primary tumor >7 cm in major diameter, confined to kidney. |
| T2a: | Primary tumor >7 cm and <10 cm in major diameter, confined to kidney. |
| T2b: | Primary tumor >10 cm in major diameter, confined to kidney. |
| T3a: | The tumor has invaded the renal vein or its segmental branches (with muscle), [and] has infiltrated the fat of the sinus; |
| T3b: | The tumor has invaded the vena cava below the diaphragm; |

TABLE 1-continued

TNM Classification

T3c: The tumor has invaded the vena cava above the diaphragm or has infiltrated the wall of the vein;
T4: The tumor has invaded beyond the Gerota's fascia.
N: Regional lymphatic ganglia:
Nx: Regional ganglia cannot be evaluated.
N0: No evidence of regional ganglia metastasis.
N1: Metastasis at the level of a single regional ganglion.
N2: Metastasis in more than one regional ganglion.
M0: No metastasis;
M1: Distant metastasis.

Grouping into stages TNM:

| Stage I | T1 | N0 | M0 |
|---|---|---|---|
| Stage II | T2 | N0 | M0 |
| Stage III | T3 | N0 | M0 |
| | T1, T2, T3 | N1 | M0 |
| Stage IV | T4 | any N | M0 |
| | any T | N2 | M0 |
| | any T | any N | M1 |

Of a total of 164 patients, 71 were selected who met the following criteria:
 Cellular histology is clear
 Tumor stage is stage I (T1N0M0) or stage II (T2N0M0)
 Fuhrman grade: Any
 Tumor size: Any, provided that the tumor is confined to the kidneys (i.e. less than or equal to T2b)
 ECOG status (Eastern Cooperative Oncology Group Performance Status): Any.
 Patients who are asymptomatic or with symptoms which are related.
Any patient with any of the following characteristics was excluded:
 Tumor stage equal to or greater than T3
 Any N+
 Any M+
 Any other histology (e.g. papillar, chromophobic, or with sarcomatoid differentiation)
 Time of monitoring less than 1 year
 Lack of sufficient data in the clinical history
 Lack of samples in paraffin for analysis of microRNA

Example 2. Analysis of the Expression of microRNAs

The tumor pieces from the nephrectomy were fixed in formalin; in particular, after a piece from a partial or radical nephrectomy was received, it was weighed, measured, and fixed by immersion in formaldehyde (10% formalin) for 24-48 hours.
Subsequently, the piece was included in paraffin, in an automatic tissue processor.
Then the piece was cut, and RNA was extracted, from the tumor samples fixed in formalin and embedded in paraffin.
The samples were hybridized with microarrays of human miRNA, version 14.0, 8×15K (Agilent Technologies), according to the manufacturer's protocol.

Example 3. Prognostication of the Risk of Relapse in CCRC Based on a Profile of miRNAs A level of statistical significance was calculated for each miRNA based on a Cox regression model (Shu, Y., Klein, J. P., and Zhang, M-J., 2007, Asymptotic theory for the Cox semi-Markov illness-death model. *Lifetime Data Anal.*, March; 13(1):91-117), with the objective of ascertaining a profile of miRNAs the expression of which bears a significant relation to survival free from the disease. The miRNAs related to disease free survival were "filtered" based on their p values. Micro RNAs (miRNAs) showing a p value <0.01 were used to develop prediction models of the risk of relapse, using the method of supervised principal components. Additionally, the correlation between the miRNAs selected was evaluated, in order to establish correlation groups so as to be able find reduced profiles. Cross-validation was employed to evaluate the exactitude of prediction of the profiles. The cut-off point was established a priori; and, to test the statistical significance, the value of p in the log rank test for the risk groups was evaluated, using 10,000 aleatory permutations.

A prediction model for progression in patients with CCRC diagnosed in stages I and II (RCC-9miR score) was generated. This model is comprised of the expression of the nine miRNAs (Table 2). The prediction score is calculated by the following formula:

$$\Sigma_i w_i x_i - 2,896,583,$$

where $w_i$ is the weight, and $x_i$ is the expression value of the microRNA i.

The result of the formula is a value which depends on the levels of expression of the microRNAs hsa-miR-223, hsa-miR-103, hsa-miR-107, hsa-miR-425, hsa-miR-340, hsa-miR-130b, hsa-miR-652, hsa-miR-214, and hsa-miR-204, having sequences identified by the sequences SEQ ID NO: 1-9.

TABLE 2

Prediction values of the 9 miRNAs:

| miRNA | p | $w_i$ (weight) |
|---|---|---|
| hsa-miR-223 | 0.0013 | 0.098392 |
| hsa-miR-103 | 0.0026 | 0.045806 |
| hsa-miR-107 | 0.0076 | 0.045869 |
| hsa-miR-425 | 0.0083 | 0.163188 |
| hsa-miR-340* | 0.0107 | 0.495063 |
| hsa-miR-130b | 0.0108 | 0.374902 |
| hsa-miR-652 | 0.0152 | 0.311327 |
| hsa-miR-214 | 0.0163 | −0.064772 |
| hsa-miR-204 | 0.0173 | −0.220399 |

Table 3 illustrates the association between the miRNA profile and progression of the disease. The association of the miRNA profile with progression of the disease is statistically significant, with p=0.0001.

TABLE 3

Contingency table, of miRNA profile versus progression of the disease:

| | Progression | | |
|---|---|---|---|
| | Yes n (%) | No n (%) | P |
| Low risk | 3 (6%) | 47 (94%) | 0.0001 |
| High risk | 9 (42.8%) | 12 (57.2%) | |

Patients with a score greater than 0.954 are regarded as high risk. The model assessed 30% of the patients as high risk. The 5-year disease-free survival (DFS) was 93.9% for low risk patients and 61.54 for high risk patients (hazard ratio HR=12.1, p=0.0001) (confidence interval CI=3.012-37.92). These difference in the long-rank test were validated with 10,000 permutations (p>0.0013). The 5-year cancer-specific survival was 95.7% for the low risk group and 86.4% for the high risk group ((HR=7.7, p=0.0084) (CI=1.687-35.14).

The 9-miRNA predictor is an excellent predictor of progression of the disease. The 9-miRNA predictor has been used as a predictive factor, and is statistically significant (p=0.023, HR=6.55, 95% CI=1.29=33.165) in the analysis of cancer-specific survival (CSS).

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A prognostic method for determining the risk of relapse of renal cancer of the clear cell renal carcinoma (CCRC) type, stages I and II, in a human subject; comprising:
   (a) determining, in a renal tumor sample biopsy from the human subject, the levels of expression of each of hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9;
   (b) determining a value which depends on the levels of expression of said microRNAs;
   (c) determining the risk of relapse in renal cancer of the CCRC type, in stages I and II, in the said human subject, by comparing the value obtained in step (b) with a cut-off value.

2. The prognostic method according to claim 1, wherein the level of expression of said microRNAs is determined with the use of at least one microarray of microRNAs.

3. A prognostic and treatment method for determining the risk of relapse of renal cancer of the CCRC type, stages I and II, in a human subject and subsequently treating said subject, the method comprising:
   (a) determining, in a renal tumor sample biopsy from the human subject, the level of expression of each of the microRNAs: hsa-miR-223, hsa-miR-103, hsa-miR-107, hsa-miR-425, hsa-miR-340, hsa-miR-130b, hsa-miR-652, hsa-miR-214, and hsa-miR-204 with sequences identified by the sequences SEQ ID NOs: 1-9;
   (b) determining a value which depends on the levels of expression of said microRNAs;
   (c) determining the risk of relapse in renal cancer of the CCRC type, in stages I and II, in the said human subject, by comparing the value obtained in step (b) with a cut-off value, and
   (d) obtaining a value in step (b) that is greater than said cut-off value, classifying said human subject as being at high risk of relapse of renal cancer of the CCRC type and subsequently administering a therapeutically effective amount of sunitinib, sorafenib, everolimus, axitinib, and/or temsirolimus to said human subject as an adjuvant therapy.

* * * * *